United States Patent
Arezi et al.

(10) Patent No.: US 10,240,196 B2
(45) Date of Patent: Mar. 26, 2019

(54) TRANSPOSASE-RANDOM PRIMING DNA SAMPLE PREPARATION

(71) Applicant: AGILENT TECHNOLOGIES, INC., Santa Clara, CA (US)

(72) Inventors: Bahram Arezi, Carlsbad, CA (US); Michael Borns, Escondido, CA (US); Holly Hogrefe, San Diego, CA (US); Connie Hansen, San Diego, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 333 days.

(21) Appl. No.: 15/167,823

(22) Filed: May 27, 2016

(65) Prior Publication Data

US 2017/0342483 A1    Nov. 30, 2017

(51) Int. Cl.
| | | |
|---|---|---|
| *C12P 19/34* | (2006.01) | |
| *C12Q 1/6874* | (2018.01) | |
| *C12Q 1/6806* | (2018.01) | |
| *C12Q 1/6869* | (2018.01) | |

(52) U.S. Cl.
CPC ......... *C12Q 1/6874* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 2010/0120098 A1 | 5/2010 | Grunenwald et al. | |
| 2013/0079251 A1* | 3/2013 | Boles | C12M 45/09 506/26 |
| 2013/0203605 A1* | 8/2013 | Shendure | C12N 15/1093 506/2 |
| 2015/0051088 A1* | 2/2015 | Kim | C12N 15/1086 506/4 |
| 2015/0051116 A1* | 2/2015 | Kim | C12N 15/1086 506/26 |
| 2015/0176071 A1 | 6/2015 | Fisher et al. | |
| 2015/0259736 A1 | 9/2015 | Steemers et al. | |
| 2015/0353925 A1 | 12/2015 | Grunenwald et al. | |

(Continued)

FOREIGN PATENT DOCUMENTS

| | | |
|---|---|---|
| WO | WO2010048605 A1 | 4/2010 |
| WO | WO2015069374 A1 | 5/2015 |

(Continued)

OTHER PUBLICATIONS

McCoy et al., Illumina TruSeq Synthetic Long-Reads Empower De Novo Assembly and Resolve Complex, Highly-Repetitive Transposable Elements, PLOS ONE, vol. 9, Issue 9, pp. 1-13, Sep. 2014. (Year: 2014).*

(Continued)

*Primary Examiner* — Kenneth R Horlick (57) ABSTRACT

Provided herein, among other things, are a variety of methods for transposase-mediated tagging and amplification of short DNA fragments, e.g., between about 150 bp and 1.5 Kb in length. In some aspects, the method includes tagging the DNA fragments with a first primer sequence using barcoded transposases followed by a primer extension reaction to introduce a second primer sequence, e.g., using random or gene-specific primers. Kits for performing this method are also provided.

17 Claims, 4 Drawing Sheets

Specification includes a Sequence Listing.

(56) References Cited

U.S. PATENT DOCUMENTS

2017/0175182 A1* 6/2017 Peter .................... C12Q 1/6874
2018/0087050 A1* 3/2018 Zheng ................ C12N 15/1068

FOREIGN PATENT DOCUMENTS

| WO | WO2015106890 A1 | 7/2015 |
| WO | WO2015113725 | 8/2015 |
| WO | WO2016003814 | 1/2016 |
| WO | WO2016168351 A1 | 4/2016 |
| WO | WO2016172373 A1 | 10/2016 |

OTHER PUBLICATIONS

Gorbacheva, et al. "Improved transposon-based library preparation for the Ion Torrent platform", BioTechniques, vol. 58, No. 4, Apr. 2015, pp. 200-202.
Nextera, "Nextera™ Technology for NGS DNA Library Preparation: Simultaneous Fragmentation and Tagging by In Vitro Transposition", www.EpiBio.com, vol. 16-3, Oct. 2009, pp. 1-6.
International Search Report and Written Opinion dated Jul. 19, 2017 for International Patent Application No. PCT/US2017/028200.

* cited by examiner

| FFPE Sample | Tx (ng) | 1st Strand Cycles | % Reads kept | % Reads unmapped | % Duplicates | % on Target | 1X Coverage | 10X Coverage | 20X Coverage |
|---|---|---|---|---|---|---|---|---|---|
| Lung Tumor FFPE | 100ng | 4 | 92.83 | 4.43 | 19.75 | 62.69 | 97.36 | 75.93 | 60.13 |
| Lung Tumor FFPE | 100ng | 4 | 92.76 | 4.5 | 19.00 | 62.42 | 97.30 | 76.34 | 60.00 |
| Lung Tumor FFPE | 100ng | 0 | 91.46 | 5.33 | 29.25 | 59.11 | 97.86 | 77.92 | 60.07 |
| Lung Tumor FFPE | 100ng | 0 | 91.35 | 6.33 | 29.43 | 59.19 | 97.83 | 78.41 | 60.41 |

FIG. 5

| FFPE Sample | Tx (ng) | 1st Strand Cycles | % Reads kept | % Reads unmapped | % Duplicates | % on Target | 1X Coverage | 10X Coverage | 20X Coverage |
|---|---|---|---|---|---|---|---|---|---|
| Breast Tumor FFPE | 100ng | 0 | 90.08 | 7.86 | 21.21 | 55.04 | 97.41 | 75.66 | 58.63 |
| Breast Tumor FR | 100ng | 0 | 90.94 | 7.01 | 23.99 | 52.04 | 98.42 | 79.34 | 60.96 |
| Gastric Tumor FFPE | 100ng | 0 | 88.17 | 8.83 | 39.11 | 47.55 | 90.71 | 57.26 | 39.88 |
| Gastric Tumor FR | 100ng | 0 | 90.53 | 7.49 | 21.98 | 57.88 | 98.31 | 73.89 | 62.43 |
| Breast Tumor FFPE* | 100ng | 0 | 91.39 | 6.51 | 23.59 | 56.05 | 97.76 | 73.70 | 60.94 |
| Breast Tumor FR* | 100ng | 0 | 92.97 | 5.19 | 22.72 | 55.79 | 98.40 | 82.26 | 65.00 |
| Gastric Tumor FFPE* | 100ng | 0 | 90.37 | 6.75 | 41.85 | 48.30 | 91.87 | 59.52 | 41.13 |
| Gastric Tumor FR* | 100ng | 0 | 92.52 | 5.53 | 23.53 | 53.92 | 98.28 | 81.04 | 63.35 |

FIG. 6

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
ctgtctcttg atcacaagt                                                    19

<210> SEQ ID NO 2
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 2
gctgacgtcg agacttgtga tcaagagaca g                                      31

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gctgacgtcg agacttgtga                                                   20

<210> SEQ ID NO 4
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (30)..(33)
<223> OTHER INFORMATION: "n" is any nucleotide

<400> SEQUENCE: 4
agctgtgcgt agatgtgatc aagagacagn nnn                          33

<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 5
cggtggagct gtgcgtagat gtgatcaaga gacag                        35
```

TRANSPOSASE-RANDOM PRIMING DNA SAMPLE PREPARATION

BACKGROUND

Next-generation Sequencing (NGS) technologies have made whole-genome sequencing (WGS) routine, and various target enrichment methods have enabled researchers to focus sequencing power on the most important regions of interest. However, there is still a need for better methods of applying NGS to difficult target DNAs, such as formalin-fixed, paraffin-embedded (FFPE) solid tumor samples, cell-free or circulating tumor DNA (cfDNA/ctDNA), or damaged DNA samples. Problems associated with sequencing such targets include that the amounts of DNA can be very small, the DNA can be very short (e.g., fragmented DNA) or chemically modified, and the allele frequencies can be very low. These problems necessitate the capture of many DNA templates.

In particular, it is challenging to sequence smaller fragments of genomic DNA using transposase-based tagging methods because many of those methods require the insertion of two adjacent transposases to produce a fragment having the appropriate sequencing primer binding site on each end, and such small fragments are often not long enough to accommodate adjacent transposases. The present disclosure provides inter alia compositions and methods to improve tagging and amplifying such DNA samples for downstream analysis, e.g., next generation sequencing.

SUMMARY

Aspects of the present disclosure include methods for tagging DNA fragments in a sample that include: (a) contacting a sample comprising double stranded DNA fragments with a plurality of transposase duplexes each loaded with an adapter to produce adapter-tagged fragments, wherein the adapter comprises a duplex region comprising a transposase recognition sequence and a 5' overhang region comprising a first primer sequence; (b) performing a primer extension reaction on the adapter tagged fragments using a random primer to produce random primer extension products, wherein the random primer comprises a random 3' nucleotide sequence and a 5' nucleotide sequence comprising a second primer sequence; and (c) amplifying the random primer extension products of (b) by polymerase chain reaction (PCR) using a forward primer comprising the first primer sequence at its 3' end and a reverse primer comprising the second primer sequence at its 3' end to produce PCR amplification products. The PCR amplification products generated will include a nucleic acid sequence derived from a DNA fragment in the sample between sequences derived from the adapter and sequences derived from the random primer. It is noted that additional functional sequences and/or moieties can be present in the adapter and/or the random primer, including but not limited to: one or more barcode, one or more degenerate base region, one or more restriction site, one or more additional primer sequences, one or more detectable label, one or more capture tag, etc. In certain embodiments, the DNA fragments in the sample have an average length of less than 1 kb.

For certain applications such as when the method is applied to analyze circulating tumor DNA or DNA recovered from an FFPE section, the amount of DNA in the sample is limiting and/or relatively short. Many transposase-based library preparation methods require two insertion sites per target fragment, while the present method requires only a single insertion per target DNA. Thus, target fragments can be captured at a higher efficiency using the present method.

It is noted that in alternative embodiments, the random primer extension reaction can be replaced with (i) adding an oligo-dN tail to the top strand of the adapter-tagged fragments using a terminal transferase to produce tailed adapter-tagged fragments (the top strand is defined as the strand to which the transposase ligates the adapter sequence having the 5' overhang region) and (ii) performing a primer extension reaction on the tailed adapter-tagged fragments using a tail primer to produce tail primer extension products, wherein the tail primer comprises a 3' sequence that hybridizes to the oligo-dN tail and a 5' sequence comprising a second primer sequence. Alternatively, one or more gene specific primers may be used in the primer extension reaction to generate gene-specific extension products that have the first and second primer sequences. Such embodiments can be used to produce gene-specific libraries or for target gene enrichment.

Kits for performing the methods described herein are also provided.

Figure 3:
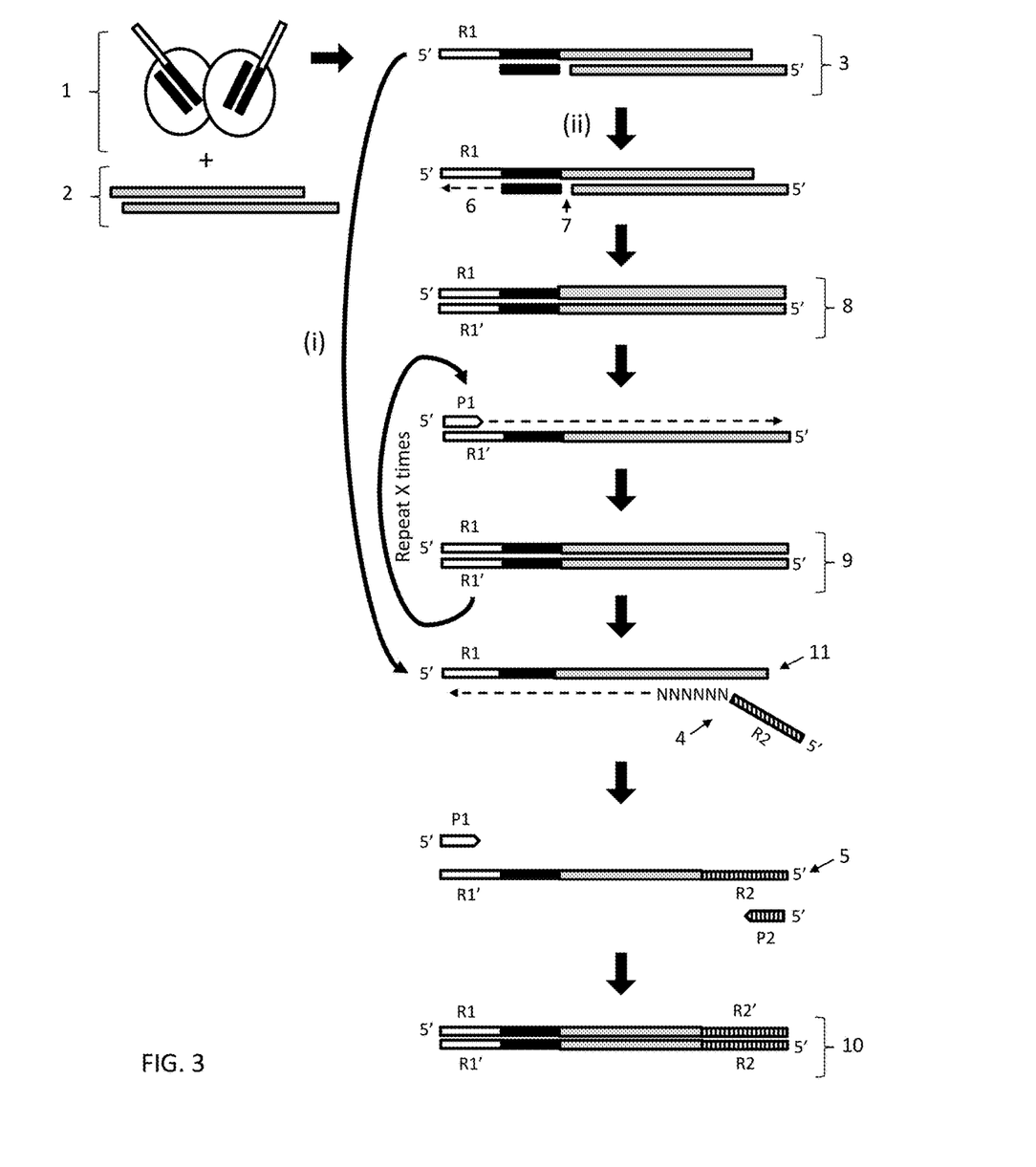
FIG. 3 schematically illustrates a method by which DNA fragments are tagged and amplified according certain aspects of the present disclosure. This embodiment employs a random primer for the primer extension reaction to produce extension products form the transposase adapter tagged fragment.

The methods described herein provide a clear advantage over current tagmentation protocols that require two transposase adapters to be added per DNA fragment. Specifically, because only a single transposase adapter is added per DNA fragment, the disclosed methods allow a user to recover genomic DNA sequences on either side of a tagmentation site, sequences that are lost in conventional transposase library preparation methods. In addition, the inclusion of a linear amplification step can overcome issues with limiting sample input (e.g., as shown in FIG. 3, option (ii)).

BRIEF DESCRIPTION OF THE FIGURES

The skilled artisan will understand that the drawings, described below, are for illustration purposes only. The drawings are not intended to limit the scope of the present teachings in any way.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry,* $5^{th}$ Ed., W. H. Freeman Pub., New York, N.Y., all of which are herein incorporated in their entirety by reference for all purposes.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections), from preserved tissue (such as FFPE sections) or from in vitro cell culture constituents, as well as samples from the environment.

The term "nucleic acid sample," as used herein denotes a sample containing nucleic acids. A nucleic acid samples used herein may be complex in that they contain multiple different molecules that contain nucleotide sequences. Genomic DNA samples from a mammal (e.g., mouse or human) are types of complex samples. Complex samples may have more than $10^4$, $10^5$, $10^6$ or $10^7$ different nucleic acid molecules. Also, a complex sample may comprise only a few molecules, where the molecules collectively have more than $10^4$, $10^5$, $10^6$ or $10^7$ or more nucleotides. A DNA target may originate from any source such as genomic DNA, or an artificial DNA construct. Any sample containing nucleic acid, e.g., genomic DNA made from tissue culture cells or a sample of tissue, may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, and uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. Thus, a primer includes a 3' nucleic acid sequence that is sufficiently complementary to a sequence in a target nucleic acid to hybridize to and act as a point of nucleic acid synthesis. Primers may also include additional sequences upstream of the 3' hybridizing sequence (e.g., a 5' sequence) that does not hybridize to the target. Such additional sequences can be for the purpose of adding regions of interest (e.g., barcodes, additional primer sequences, etc.). The sequence of nucleotides added during the extension process is determined by the sequence of the template polynucleotide. Primers can be extended, for example, by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction (or sequences that are sufficiently complementary to anneal). The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleo side triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

In the context of an adapter or a target polynucleotide, a "primer binding site" or "primer sequence" refers to a site in the adapter or target polynucleotide to which a primer (e.g., an oligonucleotide primer) hybridizes. If an oligonucleotide provides or includes a primer binding site or a primer sequence for a primer, then the primer may hybridize to that oligonucleotide or its complement (e.g., a primer binding site/primer sequence in an adapter-tagged polynucleotide).

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, Pacific Bio, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode", "barcode sequence" or "molecular barcode", as used herein, refers to a unique sequence of nucleotides used to a) identify and/or track the source of a polynucleotide in a reaction and/or b) count how many times an initial molecule is sequenced (e.g., in cases where substantially every molecule in a sample is tagged with a different sequence, and then the sample is amplified). Barcode sequences may vary widely in size and composition; the following references provide guidance for selecting sets of barcode sequences appropriate for particular embodiments: Casbon (Nuc. Acids Res. 2011, 22 e81), Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

A "degenerate base region" or "DBR" in a barcode refers to a type of molecular barcode that has complexity that is sufficient to help one distinguish between fragments to which the DBR has been added. In some cases, substantially every tagged fragment may have a different DBR sequence. In these embodiments, a high complexity DBR may be used (e.g., one that is composed of at least 10,000 or 100,000 sequences). In other embodiments, some fragments may be tagged with the same DBR sequence, but those fragments can still be distinguished by the combination of: (i) the DBR sequence, (ii) the sequence of the fragment, (iii) the sequence of the ends of the fragment, and/or (iv) the site of insertion of the DBR into the fragment. In some embodiments, at least 95%, e.g., at least 96%, at least 97%, at least 98%, at least 99% or at least at least 99.5% of the target polynucleotides become associated with a different DBR sequence. In some embodiments a DBR may comprise one or more (e.g., at least 2, at least 3, at least 4, at least 5, or 5 to 30 or more) nucleotides selected from R, Y, S, W, K, M, B, D, H, V, N (as defined by the IUPAC code).

In some cases, a DBR may be error correcting. Descriptions of exemplary error identifying (or error correcting) sequences can be found throughout the literature (e.g., in are described in US patent application publications US2010/0323348 and US2009/0105959 both incorporated herein by reference). Error-correctable codes may be necessary for quantitating absolute numbers of molecules. Many reports in the literature use codes that were originally developed for error-correction of binary systems (Hamming codes, Reed Solomon codes etc.) or apply these to quaternary systems (e.g. quaternary Hamming codes; see Generalized DNA barcode design based on Hamming codes, Bystrykh 2012 PLoS One. 2012 7: e36852).

In some embodiments, a DBR may additionally be used to determine the number of initial target polynucleotide molecules that have been analyzed, i.e., to "count" the number of initial target polynucleotide molecules that have been analyzed. PCR amplification of molecules that have been tagged with a DBR results in multiple sub-populations of products that are clonally-related in that each of the different sub-populations is amplified from a single tagged molecule. As would be apparent, even though there may be several thousand or millions or more or molecules in any of the clonally-related sub-populations of PCR products and the number of target molecules in those clonally-related sub-populations may vary greatly, the number of molecules tagged in the first step of the method can be estimated by counting the number of DBR sequences associated with a target sequence that is represented in the population of PCR products. This number is useful because, in certain embodiments, the population of PCR products made using this method may be sequenced to produce a plurality of sequences. The number of different DBR sequences that are associated with the sequences of a target polynucleotide can be counted, and this number can be used (along with, e.g., the sequence of the fragment, the sequence of the ends of the fragment, and/or the site of insertion of the DBR into the fragment) to estimate the number of initial template nucleic acid molecules that have been sequenced.

The term "sample identifier sequence" is a type of barcode that can be appended to a target polynucleotide, where the sequence identifies the source of the target polynucleotide (i.e., the sample from which sample the target polynucleotide is derived). In use, each samples is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The terms "reverse primer" and "forward primer" refer to primers that hybridize to different strands in a double-stranded DNA molecule, where extension of the primers by a polymerase is in a direction that is towards the other primer. In PCR, the forward and reverse primers used to amplify a target nucleic acid are referred to as a "primer pair".

The term "a population of DNA fragments comprising DNA fragments of less than 1 kb in length", as used herein, refers to a population of fragments in which at least 1%, at least 5%, at least 10%, at least 20%, at least 30%, at least 50%, at least 80% or at least 90% of the fragment molecules are less than 1 kb in length. In some embodiments such a population may have a median fragment length in the range of 50-500 bp, e.g., 100-400 bp.

The term "oligo-dN tail", as used herein, refers to a tail of Gs, As, Ts or Cs added onto the 3' end of a strand of a DNA molecule by the action of a terminal transferase. A tail may have 10 to more than 100 nucleotides.

The term "a primer that hybridizes to the oligo-dN tail", as used herein, refers to a primer that has an oligo-dG, oligo-dA, oligo-dT or oligo-dC tract of 8-20 or more bases at its 3' end, where those bases hybridize to a complementary homopolymeric tail added to a fragment.

The term "the sequence of a barcode", as used herein, refers to the sequence of nucleotides that makes up the barcode. The sequence of a barcode may be at least 3 nucleotides in length, in some cases from 5 to 30 or more nucleotides in length.

The term "match", as used herein, refers to an action in which two sequences are compared and if they are identical, complementary, or very similar (e.g., when error correcting barcodes are used) they are indicated as being a match. In some embodiments, matched sequences are placed into a group.

The term "assembling matched sequence reads", as used herein, refers to a computationally implemented step in which matched reads (i.e., sequences that contain the same or very similar barcode or complement thereof) are aligned with one another to produce an assembled sequence that is made up of sub-sequences that are contributed by the matched sequences reads. In some embodiments, sequence assembly may involve making consensus sequences from sequence reads that have the same barcode, and then assembling a sequence from the consensus sequences. An assembled sequence is sometimes referred to as a "contig".

The term "or variant thereof", used herein, refers to a protein that has an amino acid sequence that at least 80%, at least 85%, at least 90%, at least 95%, at least 97%, at least 98% or at least 99% identical to a protein that has a known activity, wherein the variant has at least some of the same activities as the protein of known activity. For example, a variant of a wild type transposase should be able to catalyze the insertion of a corresponding transposase into DNA.

The term "fill in reaction" or "fill in gaps" refers to an enzymatically-catalyzed reaction in which 5' overhang regions and/or internal strand breaks or gaps (missing nucleotides) in one strand of a DNA duplex are filled-in in a template-specific manner (e.g., by the action of a DNA polymerase) and, where necessary, ligated together (e.g., by the action of a DNA ligase).

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 1:
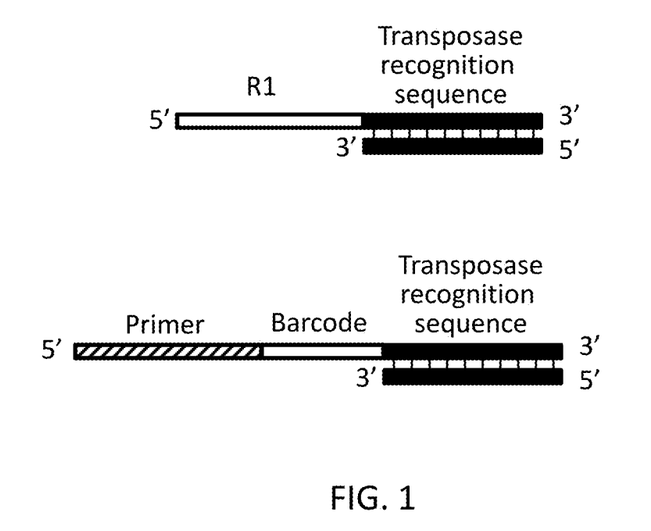
FIG. 1 schematically illustrates structural features of adapters according to aspects of the present disclosure. The adapter shown at the top of FIG. 1 includes a double stranded region that includes a transposase recognition sequence and a 5' overhang region (designated R1). The adapter shown at the bottom of FIG. 1 is similar in structure to the adapter at the top and shows two specific sequences that can be included in R1: a primer sequence and barcode.
Figure 2:
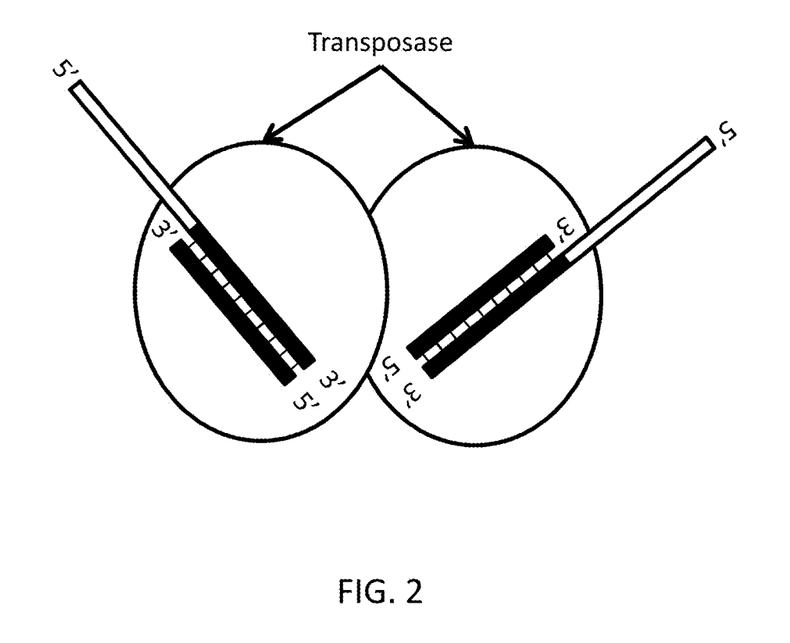
FIG. 2 schematically illustrates a transposase dimer complexed (or loaded) with two identical adapters.

Provided herein are various ways for tagging samples containing short DNA fragments using transposase dimers loaded with two identical adapters. In certain embodiments, the short DNA fragments have an average length from about 150 bp to about 1.5 Kb, including an average length of about 200 bp, 500 bp, 700 bp, 900 bp, 1 Kb, 1.2 Kb, 1.5 Kb, and anywhere there between. In some embodiments, a DNA sample is processed to obtain an average length within this range, e.g., by shearing or treating with an endonuclease. FIG. 1 shows a generic adapter (top adapter) having a double stranded region that includes a transposase recognition sequence and a 5' overhang region designated as R1 (5' and 3' ends of the strands are indicated). R1 is single stranded and can include any of a number of different functional sequences or domains. For example, the R1 region can include a primer sequence and a barcode (as shown in the bottom adapter in FIG. 1). FIG. 2 shows a transposase dimer complexed/loaded with two identical adapters.

The methods can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein in certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human.

In some embodiments, the sample comprises DNA fragments obtained from a clinical sample, e.g., form a patient that has or is suspected of having a disease or condition such as a cancer, inflammatory disease or pregnancy. In some embodiments, the sample may be made by extracting fragmented DNA from an archived patient sample, e.g., a formalin-fixed paraffin embedded (FFPE) tissue sample. In other embodiments, the patient sample may be a sample of cell-free circulating DNA from a bodily fluid, e.g., peripheral blood. The DNA fragments used in the initial steps of the method should be non-amplified DNA that has not been denatured beforehand. The sample may be fragmented mechanically (e.g., by sonication, nebulization, or shearing) or enzymatically, using a double stranded DNA fragmentase enzyme (New England Biolabs, Ipswich Mass.). In other embodiments, the DNA in the initial sample may already be fragmented (e.g., as is the case for FFPE samples and circulating cell-free DNA (cfDNA), e.g., ctDNA). The fragments in the initial sample may have a median size that is below 1 kb (e.g., in the range of 50 bp to 500 bp, 80 bp to 400 bp, or 100-1,000 bp), although fragments having a median size outside of this range may be used. Cell-free or circulating tumour DNA (ctDNA), i.e., tumour DNA circulating freely in the blood of a cancer patient, is highly fragmented, with a mean fragment size about 165-250 bp (Newman et al Nat Med. 2014 20: 548-54). cfDNA can be obtained by centrifuging whole blood to remove all cells, and then analyzing the remaining plasma.

In some embodiments (and as shown in FIG. 3), the method may comprise: contacting a sample comprising double stranded DNA fragments 2 with a plurality of transposase duplexes 1 each loaded with an adapter to produce adapter-tagged fragments (only one DNA fragment and transposase duplex are shown). In certain embodiments, the DNA fragments have an average length of less than 1 kb. The adapter includes a duplex region comprising a transposase recognition sequence (black fill, as in FIG. 1) and a 5' overhang region comprising a first primer (tag) sequence (white fill, as in FIG. 1). The amount of transposase and/or sample used may be tailored to produce a transposase insertion every 80-500 bp (e.g., every 100-300 bp) so that a relatively high proportion of tagged fragments, e.g., at least 25%, at least 50%, or at least 75% of the tagged fragments, particularly smaller fragments that are less than 500 bp in length, receive, on average, a single insertion. The resulting population of tagged fragments 3 contains a population of fragments that contain a single adapter attached to one end (only one tagged DNA fragment is shown in FIG. 3). The top strand of this tagged DNA fragment includes, in a 5' to 3' orientation, the 5' overhang sequence (white fill, denoted ad R1), one strand of the transposase recognition sequence (black fill) and one strand of the DNA fragment. The bottom strand includes, in a 3' to 5' orientation, the complementary strand of the transposase recognition sequence, a gap/nick (space), and the complementary strand of the DNA fragment. Note that the untagged end of this tagged DNA fragment can be uneven (as shown) or blunt (not shown).

The transposase used in this step of the method may be a Tn transposase (e.g. Tn3, Tn5, Tn7, Tn10, Tn552, Tn903), a MuA transposase, a Vibhar transposase (e.g. from *Vibrio harveyi*), Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, TnlO, Tyl, including variants thereof. In some cases, the insertion can be facilitated and/or triggered by addition of one or more cations. The cations can be divalent cations such as, for example, $Ca^{2+}$, $Mg^{2+}$ and $Mn^{2+}$.

In certain embodiments, the next step of the method can include performing a primer extension reaction (following arrow (i) in FIG. 3) on the top strand of the adapter tagged fragments 11 using a random primer 4 to produce random primer extension products 5. The random primer comprises a random 3' sequence (denoted by "Ns" where N is any nucleotide) and a 5' sequence comprising a second primer sequence (hashed region). Extension is indicated by a dashed arrow. The preferred DNA polymerase would exhibit strand displacement or nick translation (5'-3' exo) activity to allow random primers to anneal to the very 3'end of the top strand, and synthesize full-length products while displacing shorter downstream products.

In an alternative embodiment, the primer extension reaction is performed using one or more gene specific primers instead of random primers. In these embodiments, the top strand of the adapter tagged fragments 11 are extended using a gene-specific primer (not shown) to produce gene-specific primer extension products. As such, many adapter tagged fragments will not be extended because there is no gene-specific primer that is specific for a sequence therein. The gene-specific primers include a gene-specific 3' sequence and a 5' sequence comprising a second primer sequence (similar to the random primer 4 in FIG. 3). In some embodiments, a pool of gene specific primers is used to extend one or more specific genes (or other loci) and can contain any desired number of different primers, e.g., from 2 to 10,000 different gene specific primers.

In other embodiments, prior to the random primer extension reaction (and following arrow (ii) in FIG. 3), the method can include performing an extension or extension/ligation reaction to fill in, on the bottom strand of the transposase-tagged fragments, the sequence complementary to R1 sequence and fill in the gaps (dashed arrow 6 and upward arrow 7) to form complete transposase-tagged fragment duplexes 8 (the sequence complementary to R1 is denoted R1'). These complete transposase-tagged fragment duplexes can then be subjected to a linear amplification reaction with a linear amplification primer P1 comprising the first primer sequence at its 3' end to generate duplex 9. The linear amplification reaction can be repeated (as indicated with the "Repeat" arrow), which will generate additional copies of the top strand of duplex 9 (not shown). The linear amplification reaction can be performed any desired number of times, for example between 2 and 40 times, e.g., 4 times, 10 times, 20 times, 30 times, etc.

The linear amplification products can then be subjected to a random primer extension as described above to produce random primer extension products 5.

In certain embodiments, either the adapter and/or the random primer includes a least one additional region. For example, the adapter and/or the random primer can include a barcode. The barcode can be a sample-specific barcode, i.e., a barcode that is used to identify the sample from which a DNA fragment is derived. In some embodiments, the barcode includes a degenerate base region (DBR), the use of which is described in detail above. Any combination of barcodes in the adapter and/or reverse primer can be used. In embodiments in which both the adapter and random primer include barcodes, the barcodes can be the same in the adapter and reverse primer or they may be different at one or more position, according to the desires of the user and the way in which the barcodes are to be used in downstream processes/analyses.

Next, the method includes amplifying the random primer extension products 5 by polymerase chain reaction (PCR) using a forward primer comprising the first primer sequence at its 3' end P1 and a reverse primer comprising the second primer sequence at its 3' end P2 to produce PCR amplified products 10. These products contain a sequence from a DNA fragment from the sample (in grey) and all or part of domains R1 and R2 (e.g., the parts of domains R1 and R2 that are bounded by the forward and reverse primers P1 and P2).

Figure 4:
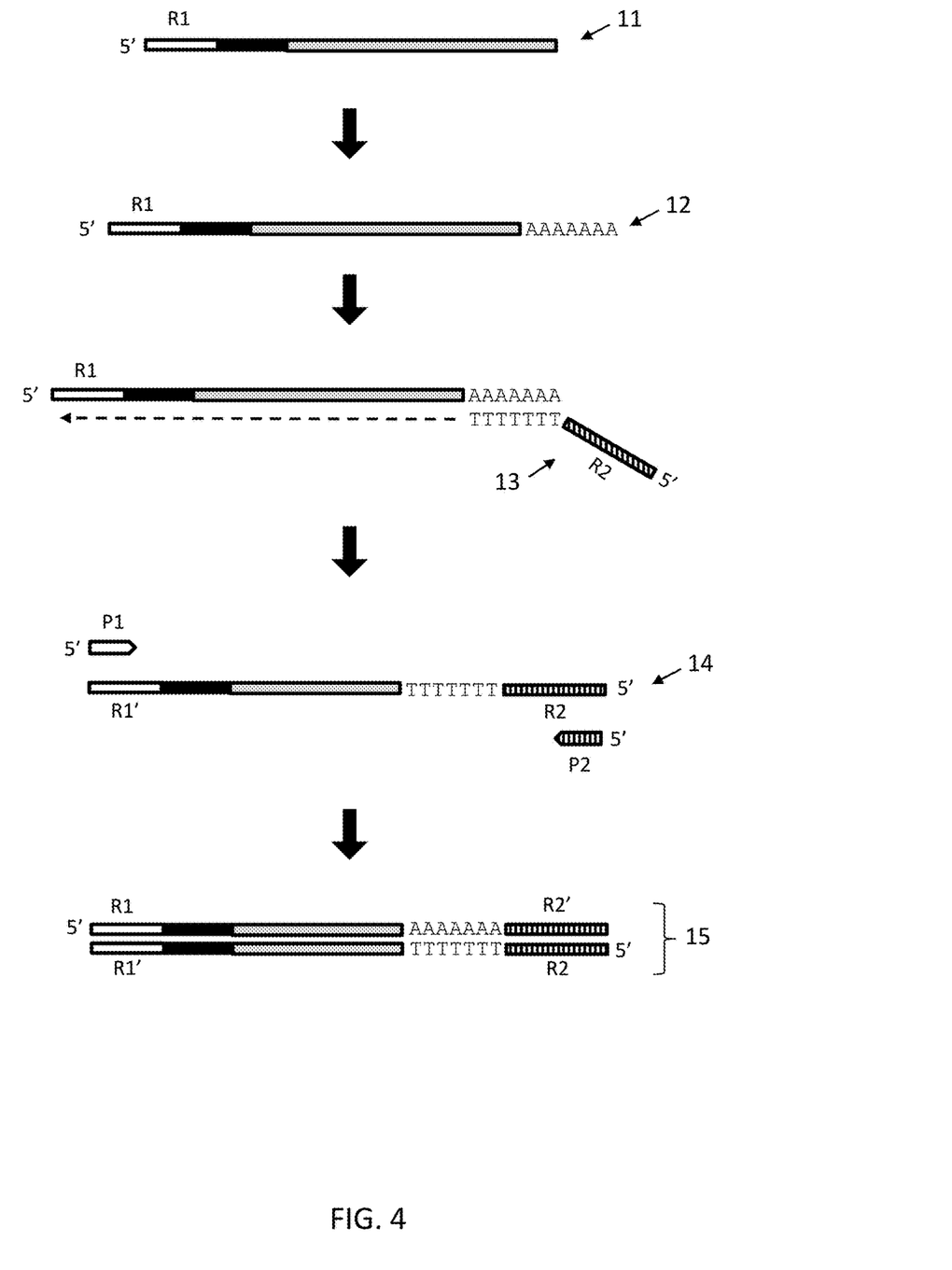
FIG. 4 schematically illustrates an embodiment in which an oligo-dA tag is added to the transposase adapter tagged fragment followed by a primer extension reaction using a tail primer having a 3' poly-dT sequence. This can replace the random primer step shown in FIG. 3.

In certain embodiments, the random primer extension reaction shown in FIG. 3 can be replaced with an alternative linear amplification process. For example, as shown in FIG. 4, the method can include adding an oligo-dN tail to the top strand of the adapter-tagged fragments 11 using a terminal transferase or a modified DNA polymerase with template-independent polymerase activity to produce tailed adapter-tagged fragments 12 (in this case, the dN tail is a poly-A tail). A primer extension reaction is then performed on the tailed adapter-tagged fragments 12 using a tail primer 13 to produce tail primer extended products 14. The tail primer includes a 3' sequence that hybridizes to the oligo-dN tail (in this case, a poly-T sequence) and a 5' sequence R2 that includes a second primer sequence P2. These tail primer extended products 14 can be amplified by polymerase chain reaction (PCR) using a forward primer comprising the first primer sequence at its 3' end P1 and a reverse primer comprising the second primer sequence at its 3' end P2 to produce PCR amplified products 15 (similar to the PCR amplification described above).

These PCR amplification products can be used for any desired downstream processes or analyses as desired by a user.

It is noted here that a user may include a sample enrichment step, a sample clean-up step, and/or an enzyme inactivation or removal step where desired. For example, an initial sample of DNA fragments may be enriched for particular target sequence(s) of interest, e.g., using a hybridization-based target enrichment (e.g., Agilent SureSelect or HaloPlex Target Enrichment). In addition, products produced in any one of the steps of the method can be purified before performing a subsequent step, e.g., amplification product purification (e.g., Agencourt AMPure Purification kits). No limitation in this regard is intended.

In certain embodiments, the method may further comprise sequencing the PCR amplification products 10. As would be apparent, in these embodiments, sequences that are compatible with a desired sequencing platform can be added to the fragments in at any convenient step in the process, e.g., as part of the adapter, the random primer, the linear amplification primer, the forward primer, or the reverse primer. As such, in embodiments where two sequencing primer sequences are used in a sequencing platform, the first sequencing primer sequence can be: (i) the first primer sequence, (ii) on a 5' tail of the forward PCR primer, or (iii) downstream of the first primer sequence in the adapter; and the second sequencing primer sequence can be: (i) the second primer sequence, (ii) on a 5' tail of the reverse primer, or (iii) downstream of the second primer sequence on the random primer. The products may be sequenced using any suitable method including, but not limited to Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

The sequencing step results in a plurality of sequence reads that includes the sequence of at least part of the sequence of a DNA fragment as well as additional sequences in the tagged DNA fragments present in the adapter and/or reverse/tail primer, e.g., the sequence of a barcode. The sequence reads can be matched and assembled to obtain assembled sequences (e.g., contigs) that represent sequences that are longer than the average sequence length of the DNA fragments in the sample. Such contigs can represent most or all of a desired polynucleotide sequence from the individual from which the initial sample was derived (e.g., a gene, a genetic locus, cDNA, etc.). As would be apparent, this part of the method may comprise comparing the barcodes in at least some of the sequence reads to one another to obtain matches, and assembling matched sequence reads to obtain the sequence of interest. In some embodiments, DNA fragments derived from different samples (e.g., from different individuals) that have a sample-specific barcode are combined at any convenient step after the barcode has been added and prior to the sequencing step. Sequences from these combined samples that include the sequence of the sample-specific barcode can be de-convoluted and assembled as desired.

In any of the methods described above, the method may further comprise determining how many DBR sequences are associated with a particular sequence, thereby providing an estimate of the number of copies of that sequence in the initial sample. Such methods are described in Casbon (Nuc. Acids Res. 2011, 22 e81) among other publications.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a transposase tagged sample may be combined with transposase tagged samples from other sources, e.g., 2 or more sources, 3 or more sources, 5 or more sources, 10 or more sources, 50 or more sources, 100 or more sources, 500 or more sources, 1000 or more sources, 5000 or more sources, up to and including about 10,000 or more sources, where the molecular barcode of the transposase allows the sequences from different sources to be distinguished after they are analyzed.

As would be recognized, some of the analysis steps of the method, e.g., the comparing and assembly steps, can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

Kits

Also provided by this disclosure are kits for practicing the subject method, as described above. In certain embodiments, the kit may comprise a plurality of transposase duplexes each loaded with an adapter (or separate transposase and adapter reagents to make such duplexes), where the adapter includes a duplex region having a transposase recognition sequence and a 5' overhang region with a first primer sequence; a random primer having a random 3' sequence and a 5' sequence with a second primer sequence, or a tail primer having a 3' sequence that hybridizes to an oligo-dN tail and a 5' sequence with the second primer sequence; a forward primer having the first primer sequence at its 3' end; and a reverse primer having the second primer sequence at its 3' end. In some embodiments, the kit can include multiple different adapters in separate containers, where each different adapter has a difference barcode sequence to tag DNA fragments from different samples. The kit can include additional reagents for performing any of the methods described herein. For example, the kit can include enzymes (e.g., a ligase, a polymerase, a thermostable polymerase, a terminal transferase etc.), nucleotides, buffers, nucleic acid purification reagents, etc.

The various components of the kit may be present in separate containers or certain compatible components may be precombined into a single container, as desired. In addition to the reagents described above, a kit may contain any of the additional components used in the method described above, e.g., one or more enzymes and/or buffers, etc.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Materials and Methods

Sample DNA Fragmentation and Insertion of R1 Adaptor Sequence

Transposase loading sequences: (1A) 5'-CTGTCTCTT-GATCACAAGT-3' (SEQ ID NO:1); 5'-GCTGACGTCGA-GACTTGTGATCAAGAGACAG-3' (SEQ ID NO:2). 100 ng of transposase loaded with (1A) is mixed with 10 ng of sample DNA in SureSelect$^{QXT}$ buffer (Agilent Technologies P/N 5190-7053). The samples are then incubated at 42° C. for 10 minutes. Cool samples to 4° C. then add 32 µl of SureSelect$^{QXT}$ stop solution (Agilent Technologies P/N 5190-7059) and incubate for 1 minute at room temperature. Clean up samples: bind sample DNA with 50 µl of Agencourt AMPure XP beads (Beckman Coulter P/N A63882) and wash twice with 70% ethanol, dry on a heated block at 37° C. and elute DNA in 20 µl of water.

First Strand Linear Cycling with 1A

First strand linear cycling primer: 5'-GCTGACGTCGA-GACTTGTGA-3' (SEQ ID NO:3). Reaction setup (500): 17.5 µl of water, 10 µl of Herculase II Fusion PCR reaction buffer (Agilent Technologies P/N 600675-52), 0.5 µl dNTP's 200 µM each (Agilent Technologies P/N 200415-51), 2 µM first strand linear cycling primer, 1 µl Herculase II Fusion DNA Polymerase (Agilent Technologies P/N 600672-51), and 20 µl fragmented sample DNA. Cycling parameters: 68° C. for 8 minutes; 98° C. for 2 minutes; 98° C. for 30 seconds, 57° C. for 30 seconds, and 72° C. for 1 minute (4 cycles), 72° C. for 5 minutes. Clean up samples: bind sample DNA with 50 µl of Agencourt AMPure XP beads (Beckman Coulter P/N A63882) and wash twice with 70% ethanol, dry on a heated block at 37° C. and elute DNA in 20 µl of water.

Second Strand Reaction and Insertion of R2 Adaptor Sequence

Second strand random primer sequence: 5'-AGCTGT-GCGTAGATGTGATCAAGAGACAGNNNN-3' (SEQ ID NO:4). Reaction setup (500): 23 µl of water, 5 µl NEBuffer 2 (New England Biolabs P/N B7002S), 0.5 µl dNTP's (Agilent Technologies P/N 20045-51), 0.5 µl second strand random primer (100 µM), 20 µl first strand linear cycled DNA or 20 µl of fragmented sample DNA, and 1 µl exo (−) Klenow fragment (Agilent Technologies bulk enzyme 50 U/µl) added after denaturation. Cycling parameters: 95° C. for 2 minutes, 4° C. for 15 minutes; 4° C.+1° C. per cycle (32 cycles); 37° C. for 1 hour and 30 minutes; 70° C. for 10 minutes. Clean up samples: bind sample DNA with 50 µl of Agencourt AMPure XP beads (Beckman Coulter P/N A63882) and wash twice with 70% ethanol, dry on a heated block at 37° C. and elute DNA in 20 µl of water.

PCR Amplification of Second Strand DNA Using R1 and R2 Primers

Forward R1 primer: 5'-GCTGACGTCGAGACTT-GTGA-3' (SEQ ID NO:3); Reverse R2 primer: 5'-CGGTG-GAGCTGTGCGTAGATGTGATCAAGAGACAG-3' (SEQ ID NO:5). Reaction setup (500): 18.25 µl of water, 10 µl of Herculase II Fusion PCR reaction buffer (Agilent Technologies P/N 600675-52), 0.5 µl dNTP's 200 µM each (Agilent Technologies P/N 200415-51), 0.2504 each forward and reverse primer, 1 µl Herculase II Fusion DNA Polymerase (Agilent Technologies P/N 600672-51), and 20 µl of second strand DNA. Cycling parameters: 98° C. for 2 minutes; 98° C. for 30 seconds, 56° C. for 30 seconds, and 72° C. for 1 minute (14 cycles), 72° C. for 5 minutes. Clean up samples: bind sample DNA with 50 µl of Agencourt AMPure XP beads (Beckman Coulter P/N A63882) and wash twice with 70% ethanol, dry on a heated block at 37° C. and elute DNA in 13 µl of water. Target enrichment was carried out using SureSelect$^{QXT}$ Target Enrichment Kit (Agilent Technologies P/N G9681B).

Data Definitions

Figure 5:
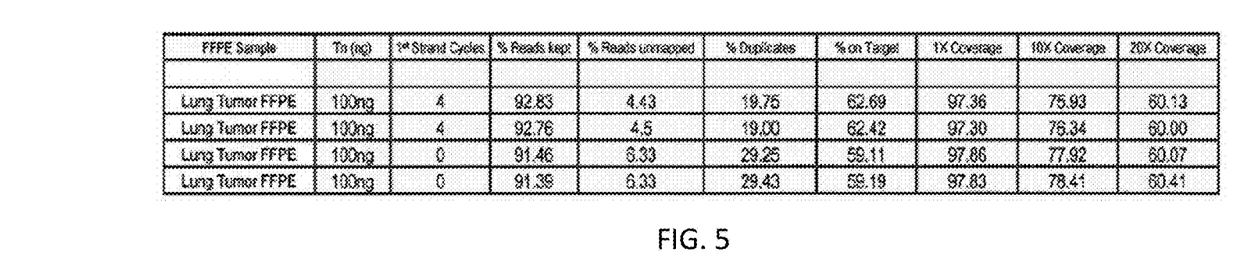
FIG. 5 is a table showing results of sequence analysis of lung tumor DNA fragments from FFPE samples (see Example 1).
Figure 6:
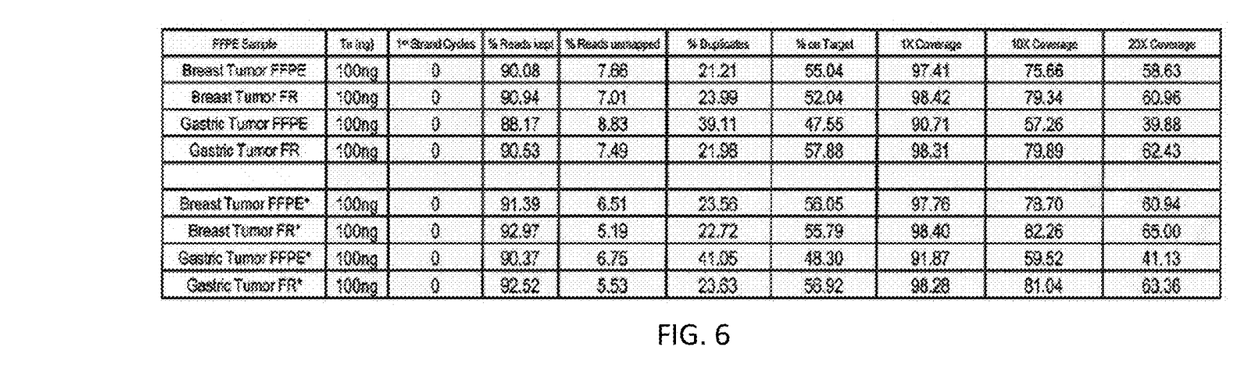
FIG. 6 is a table showing results of sequence analysis of breast tumor and gastric tumor DNA fragments from FFPE samples (see Example 2).

The tables in FIGS. 5 and 6 include the following information: Tn (ng)=ng amount of loaded transposase used in each 50 µl DNA fragmentation reaction; 1$^{st}$ strand cycles=number of first stand cycles; % reads kept=percent of reads that map to the reference genome after filtering; % reads unmapped=percent of reads that don't map to the reference genome and low quality reads; % duplicates=percent of mapped sequence that is marked as duplicate and not unique; % on target=percent of aligned reads that map back to the capture bait library or the targeted region of the genome; coverage 1×, 10×, 20×=The percentage of bases that attained at least 1×, 10×, or 20× coverage. At higher levels of coverage, each base is covered by a higher number of aligned sequence reads, so base calls can be made with a greater level of confidence.

Example 1:

Lung Tumor FFPE DNA Fragment Tagging—1$^{st}$ Strand Synthesis Cycles and Barcoding The first strand enrichment method can be performed with molecular-barcoding of the ES sequence.

Methods: 10 ng FFPE/FR DNA Input ClearSeq Comprehensive Cancer Panel, 0.8 million reads, 2×100 bp, 12 Pre-hyb PCR cycles.

Sequencing results are summarized in FIG. 5. Methods using 4 cycles of first strand synthesis have complexity that is improved, % duplicates are reduced, % on target is increased. This demonstrates that better sequencing results are generated.

Example 2:

Breast Tumor and Gastric Tumor FFPE DNA Fragment Tagging—No 1$^{st}$ Strand Synthesis Cycles and No Barcoding Methods: 10 ng FFPE/FR DNA Input, ClearSeq Comprehensive Cancer Panel, 0.8 million reads, 2×100 bp, 12 Pre-hyb PCR cycles.

Sequencing results are summarized in FIG. 6. Methods without a first strand cycling or using barcoding show high coverage.

EMBODIMENTS

Non-limiting examples of certain embodiments of the present disclosure are provided below.

1. Aspects of the present disclosure include method comprising: (a) contacting a sample comprising double stranded DNA fragments having an average length of from 150 bp to 1.5 Kb with a plurality of transposase duplexes each loaded with an adapter to produce adapter-tagged fragments, wherein the adapter comprises a duplex region comprising a transposase recognition sequence and a 5' overhang region comprising a first primer sequence; (b) performing a primer extension reaction on the adapter tagged fragments using a random primer to produce random primer extension products, wherein the random primer comprises a random 3' sequence and a 5' sequence comprising a second primer sequence; (c) amplifying the random primer extension products of (b) by polymerase chain reaction (PCR) using a forward primer comprising the first primer sequence at its 3' end and a reverse primer comprising the second primer sequence at its 3' end to produce PCR amplification products.

2. The method of embodiment 1, wherein prior to step (b) the method further comprises: (i) performing an extension or extension/ligation reaction on the adapter tagged fragments to fill in the 5' overhang region and fill in gaps of the adapter tagged fragments; and (ii) performing at least one linear amplification reaction with a linear amplification primer comprising the first primer sequence at its 3' end.

3. The method of embodiment 2, wherein step (ii) comprises performing between 2 and 30 linear amplification reactions.

4. The method of embodiment 1, wherein: the first primer sequence is a first sequencing primer sequence, the forward primer comprises a 5' tail comprising a first sequencing primer sequence, or the adapter further comprises a first sequencing primer sequence downstream of the first primer sequence; and the second primer sequence is a second sequencing primer sequence, the reverse primer comprises a 5' tail comprising a second sequencing primer sequence, or the random primer further comprises a second sequencing primer sequence downstream of the second sequencing primer sequence.

5. The method of embodiment 4, wherein the first and second sequencing primer sequences are for next generation sequencing applications.

6. The method of embodiment 4, wherein: the adapter further comprises a barcode downstream of the first sequencing primer sequence; and/or the random primer further comprises a barcode downstream of the second sequencing primer sequence.

7. The method of embodiment 6, wherein the barcode in the adapter and/or random primer is a sample-specific barcode.

8. The method of embodiment 6, wherein the barcode in the adapter and/or random primer comprises a degenerate base region (DBR).

9. The method of any one of embodiments 4 to 8, further comprising sequencing the PCR amplification products to obtain sequence reads for at least a subset of DNA fragments in the sample and assembling the sequence reads into contigs.

10. The method of embodiment 1, wherein the sample of DNA fragments is isolated from a clinical sample.

11. The method of embodiment 10, wherein the clinical sample is cell-free DNA extracted from a bodily fluid.

12. The method of embodiment 11, wherein the bodily fluid is blood.

13. The method of embodiment 10, wherein the clinical sample is a formalin-fixed and paraffin embedded (FFPE) sample.

14. Aspects of the present disclosure include methods comprising: (a) contacting a sample comprising double stranded DNA fragments having an average length of less than 1 kb with a plurality of transposase duplexes each loaded with an adapter to produce adapter-tagged fragments, wherein the adapter comprises a duplex region comprising a transposase recognition sequence and a 5' overhang region comprising a first primer sequence; (b) adding an oligo-dN tail to the top strand of the adapter-tagged fragments using an enzyme with terminal transferase activity to produce tailed adapter-tagged fragments; (c) performing a primer extension reaction on the tailed adapter-tagged fragments using a tail primer to produce tail primer extension products, wherein the tail primer comprises a 3' sequence that hybridizes to the oligo-dN tail and a 5' sequence comprising a second primer sequence; (d) amplifying the tail primer extension products of (c) by polymerase chain reaction (PCR) using a forward primer comprising the first primer sequence at its 3' end and a reverse primer comprising the second primer sequence at its 3' end to produce PCR amplification products.

15. The method of embodiment 14, further comprising sequencing the PCR amplification products to obtain sequence reads for at least a subset of DNA fragments in the sample and assembling the sequence reads into contigs.

16. The method of embodiment 14, wherein the sample of DNA fragments is isolated from a clinical sample, wherein the clinical sample is a formalin-fixed and paraffin embedded (FFPE) sample.

17. Aspects of the present disclosure include kits comprising: a plurality of transposase duplexes each loaded with an adapter, wherein the adapter comprises a duplex region comprising a transposase recognition sequence and a 5' overhang region comprising a first primer sequence; a random primer comprising a random 3' sequence and a 5' sequence comprising a second primer sequence, or a tail primer comprising a 3' sequence that hybridizes to an oligo-dN tail and a 5' sequence comprising the second primer sequence; a forward primer comprising the first primer sequence at its 3' end; a reverse primer comprising the second primer sequence at its 3' end; and one or more additional reagents for performing the method of embodiment 1 or 14.

The invention claimed is:

1. A method comprising:
   (a) contacting a sample comprising double stranded DNA fragments having an average length of from 150 bp to 1.5 Kb with a plurality of transposase duplexes each loaded with an adapter to produce adapter-tagged fragments, wherein the adapter comprises a duplex region comprising a transposase recognition sequence and a 5' overhang region comprising a first primer sequence;
   (b) performing a primer extension reaction on the adapter tagged fragments using a random primer to produce random primer extension products, wherein the random primer comprises a random 3' sequence and a 5' sequence comprising a second primer sequence;
   (c) amplifying the random primer extension products of (b) by polymerase chain reaction (PCR) using a forward primer comprising the first primer sequence at its 3' end and a reverse primer comprising the second primer sequence at its 3' end to produce PCR amplification products.

2. The method of claim 1, wherein prior to step (b) the method further comprises:
   (i) performing an extension or extension/ligation reaction on the adapter tagged fragments to fill in the 5' overhang region and fill in gaps of the adapter tagged fragments; and
   (ii) performing at least one linear amplification reaction with a linear amplification primer comprising the first primer sequence at its 3' end.

3. The method of claim 2, wherein step (ii) comprises performing between 2 and 30 linear amplification reactions.

4. The method of claim 1, wherein:
   the first primer sequence is a first sequencing primer sequence, the forward primer comprises a 5' tail comprising a first sequencing primer sequence, or the adapter further comprises a first sequencing primer sequence downstream of the first primer sequence; and
   the second primer sequence is a second sequencing primer sequence, the reverse primer comprises a 5' tail comprising a second sequencing primer sequence, or the random primer further comprises a second sequencing primer sequence downstream of the second primer sequence.

5. The method of claim 4, wherein the first and second sequencing primer sequences are for next generation sequencing applications.

6. The method of claim 4, wherein:
   the adapter further comprises a barcode downstream of the first sequencing primer sequence; and/or
   the random primer further comprises a barcode downstream of the second sequencing primer sequence.

7. The method of claim 6, wherein the barcode in the adapter and/or random primer is a sample-specific barcode.

8. The method of claim 6, wherein the barcode in the adapter and/or random primer comprises a degenerate base region (DBR).

9. The method of claim 4, further comprising sequencing the PCR amplification products to obtain sequence reads for at least a subset of DNA fragments in the sample and assembling the sequence reads into contigs.

10. The method of claim 1, wherein the sample of DNA fragments is isolated from a clinical sample.

11. The method of claim 10, wherein the clinical sample is cell-free DNA extracted from a bodily fluid.

12. The method of claim 11, wherein the bodily fluid is blood.

13. The method of claim 10, wherein the clinical sample is a formalin-fixed and paraffin embedded (FFPE) sample.

14. A method comprising:
   (a) contacting a sample comprising double stranded DNA fragments having an average length of less than 1 kb with a plurality of transposase duplexes each loaded with an adapter to produce adapter-tagged fragments, wherein the adapter comprises a duplex region comprising a transposase recognition sequence and a 5' overhang region comprising a first primer sequence;
   (b) adding an oligo-dN tail to the top strand of the adapter-tagged fragments using an enzyme with terminal transferase activity to produce tailed adapter-tagged fragments;
   (c) performing a primer extension reaction on the tailed adapter-tagged fragments using a tail primer to produce tail primer extension products, wherein the tail primer comprises a 3' sequence that hybridizes to the oligo-dN tail and a 5' sequence comprising a second primer sequence;
   (d) amplifying the tail primer extension products of (c) by polymerase chain reaction (PCR) using a forward primer comprising the first primer sequence at its 3' end and a reverse primer comprising the second primer sequence at its 3' end to produce PCR amplification products.

15. The method of claim 14, further comprising sequencing the PCR amplification products to obtain sequence reads for at least a subset of DNA fragments in the sample and assembling the sequence reads into contigs.

16. The method of claim 14, wherein the sample of DNA fragments is isolated from a clinical sample, wherein the clinical sample is a formalin-fixed and paraffin embedded (FFPE) sample.

17. A kit comprising:
- a plurality of transposase duplexes each loaded with an adapter, wherein the adapter comprises a duplex region comprising a transposase recognition sequence and a 5' overhang region comprising a first primer sequence;
- a random primer comprising a random 3' sequence and a 5' sequence comprising a second primer sequence, or a tail primer comprising a 3' sequence that hybridizes to an oligo-dN tail and a 5' sequence comprising the second primer sequence;
- a forward primer comprising the first primer sequence at its 3' end;
- a reverse primer comprising the second primer sequence at its 3' end; and
- one or more additional reagents for performing the method of claim 1.

* * * * *

UNITED STATES PATENT AND TRADEMARK OFFICE
CERTIFICATE OF CORRECTION

PATENT NO. : 10,240,196 B2
APPLICATION NO. : 15/167823
DATED : March 26, 2019
INVENTOR(S) : Bahram Arezi et al.

Page 1 of 1

It is certified that error appears in the above-identified patent and that said Letters Patent is hereby corrected as shown below:

In the Specification

In Column 16, Line 42, delete "(500):" and insert -- (50 µl): --, therefor.

In Column 16, Line 60, delete "(500):" and insert -- (50 µl): --, therefor.

In Column 17, Line 11, delete "(500):" and insert -- (50 µl): --, therefor.

In Column 17, Line 14, delete "0.2504" and insert -- 0.25 µM --, therefor.

Signed and Sealed this
Eighteenth Day of June, 2019

Andrei Iancu
*Director of the United States Patent and Trademark Office*